United States Patent
Ahonen et al.

(10) Patent No.: US 11,449,208 B2
(45) Date of Patent: Sep. 20, 2022

(54) INTERACTIVE AND INTUITIVE METHOD TO SHAPE 3D DOSE DISTRIBUTION DURING OPTIMIZATION OF IMRT PLANS

(71) Applicant: Varian Medical Systems International AG., Cham (CH)

(72) Inventors: Risto Ahonen, Espoo (FI); Lauri Halko, Helsinki (FI); Jarkko Y. Peltola, Tuusula (FI); Mikko Vainio, Espoo (FI)

(73) Assignee: Varian Medical Systems International AG, Cham (CH)

( * ) Notice: Subject to any disclaimer, the term of this patent is extended or adjusted under 35 U.S.C. 154(b) by 0 days.

(21) Appl. No.: 15/643,148

(22) Filed: Jul. 6, 2017

(65) Prior Publication Data
US 2019/0012066 A1    Jan. 10, 2019

(51) Int. Cl.
| | | |
|---|---|---|
| G06F 3/04845 | (2022.01) | |
| G06T 19/20 | (2011.01) | |
| A61N 5/10 | (2006.01) | |
| G06F 3/0488 | (2022.01) | |

(52) U.S. Cl.
CPC ....... G06F 3/04845 (2013.01); A61N 5/1031 (2013.01); A61N 5/1048 (2013.01); G06T 19/20 (2013.01); A61N 2005/1074 (2013.01); G06F 3/0488 (2013.01); G06T 2200/24 (2013.01); G06T 2210/41 (2013.01); G06T 2219/2021 (2013.01)

(58) Field of Classification Search
None
See application file for complete search history.

(56) References Cited

U.S. PATENT DOCUMENTS

| | | | |
|---|---|---|---|
| 2002/0027971 A1* | 3/2002 | Deasy | A61N 5/1031 378/65 |
| 2010/0183121 A1 | 7/2010 | Riker et al. | |
| 2011/0107270 A1* | 5/2011 | Wang | G16H 20/40 715/850 |

(Continued)

OTHER PUBLICATIONS

Godley et al. (Accumulating daily-varied dose distributions of prostate radiation therapy with soft-tissue-based kV CT guidance, Journ Al of Applied Clinical Medical Physics, vol. 13, No. 3, 2012) (Year: 2012).*

*Primary Examiner* — Kyle Zhai (57) ABSTRACT

New techniques are described herein for providing a user-friendly interface for adjusting dose distribution values during optimization of a radiation application plan. In an embodiment, a graphical user interface is provided that provides an image of a target area for a radiation application, and a graphical overlay of a dose distribution disposed over the target area that visually represents the optimized dose distribution according to the input dose parameters. In one or more embodiments, the dose distribution may be automatically calculated from input parameters supplied by a user through the graphical user interface prior to optimization. A user (such as a clinician, radiation oncologist, or radiation therapy operator, etc.) is able to modify the visualization of the dose distribution volume during optimization via a user input device in conjunction with the graphical user interface and have the modification adjusted in real-time.

20 Claims, 6 Drawing Sheets

(56) References Cited

U.S. PATENT DOCUMENTS

| | | | |
|---|---|---|---|
| 2013/0324784 A1* | 12/2013 | Fredriksson | A61N 5/1031 600/1 |
| 2014/0201670 A1 | 7/2014 | Mallya et al. | |
| 2015/0262029 A1* | 9/2015 | Pirchheim | G06K 9/52 382/103 |
| 2016/0051840 A1* | 2/2016 | Rdemark | A61N 5/1031 600/1 |
| 2016/0303398 A1 | 10/2016 | Eriksson | |

* cited by examiner

Exemplary Computer System 600

Figure 6

INTERACTIVE AND INTUITIVE METHOD TO SHAPE 3D DOSE DISTRIBUTION DURING OPTIMIZATION OF IMRT PLANS

COPYRIGHT NOTICE

The patent or application file contains at least one drawing executed in color. Copies of this patent or patent application publication with color drawing(s) will be provided by the Office upon request and payment of the necessary fee.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of this invention relate generally to radiation application planning procedures. More specifically, embodiments of this invention are directed to interactive modeling of dose distribution objectives in a graphical user interface.

BACKGROUND OF THE INVENTION

In radiation therapy, accurately identifying and delineating anatomic structures during the treatment planning phase is critically important. The objective of every such procedure is to provide an accurate definition of a target volume and any organs at risk in order to deliver the maximum radiation dose to the target volume (e.g., tumor) while sparing the surrounding healthy tissue from being subject to exposure to potentially harmful radiation.

During the planning stage, typically the treatment planner defines a plan to deliver radiation at calculated dosages to targeted areas and structures/organs. The plan may be defined as one or more dose objectives, which include parameters that limit the scope of the radiation application. These parameters are typically generated by automated software applications as data values, and may be expressed as a dose-volume histogram (DVH) curve that plots the expected amount of radiation received in one or more structures at or near targeted areas. Commonly, optimization may be performed for the calculated dose distributions, to for example, calculate a more even dose distribution, and to apply further constraints—such as lower and upper radiation limits for certain areas or structures, for example. While a useful tool for conveying dose distribution data efficiently, DVH curves are two-dimensional representations, and as such, any three dimensional data corresponding to the planned dose would be lost in such a representation.

In addition to DVH curves, planned dose distribution applications may also be expressed as three-dimensional dose distribution volumes, which plot (over multiple two-dimensional image "slices") the expected volume encompassed by a radiation application within computer-generated images of the target area. These volumes are typically presented as an overlay on top of the images of the target area to allow the treatment planner to visually verify that the desired structures are included. However, the size and shape of the radiation application volumes are static for each calculated dose distribution. As such, adjusting the dosage for one portion of a structure would invalidate the DVH and require a recalculation of the dose distribution. A similar issue arises when "hot spots" are created. Hot spots are regions that are unintentionally calculated (typically as a result of incomplete or conflicting optimization parameters) to receive an undesirably high amount of dose at one or more locations. While the unintended allocation of dosage may not be important when directed to non-critical tissue (such as fat), the dose distribution may require recalculation to ensure patient safety when the hot spots happen to target otherwise healthy tissues or organs. Similarly, cold spots may occur (also as a result of incomplete or conflicting optimization parameters), in which a dose distribution is calculated to deliver an insufficient amount of radiation to a structure or area. Because the distributions and dose distribution volumes are static, any modification or adjustment to the dose values (to reapportion radiation between hot and cold spots, for example) could not be performed by available solutions.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

To overcome the difficulties inherent in conventional dose distribution optimization applications, new techniques are described herein for providing a user-friendly interface for adjusting dose distribution values during optimization of a radiation application plan. In an embodiment, a graphical user interface is provided that provides an image of a target area for a radiation application, and a graphical overlay of a volumetric dose objective and optimized dose distribution disposed over the target area that visually represents the planned dose distribution according to the input dose parameters. In one or more embodiments, the dose distribution may be automatically calculated from input parameters supplied by a user through the graphical user interface prior to optimization. A user (such as a clinician, radiation oncologist, or radiation therapy operator, etc.) is able to modify the visualization of the dose distribution volume during optimization via a user input device in conjunction with the graphical user interface.

In one or more embodiments, the user is able to modify the dose distribution volume directly by enacting a deformation operation through actuation of a user input device at a position in the graphical representation of the dose distribution volume where modification is desired. For example, using a mouse or stylus input device, a user is able to actuate a first position enclosed by the distribution volume to begin the deformation process. The user is then able to specify an end location of the deformation process by actuating a second position in the image that lies outside of the space enclosed by the original distribution volume. The dose distribution volume is thereafter warped or "deformed" between the first and second positions to enclose the second position and all points in between the first and second position (e.g., along a straight line).

According to another aspect, a method is provided for automatically deforming a volumetric dose objective calculated for a dose distribution during optimization. The method includes receiving an initial set of dose objectives for a target area in a radiation application subject, either from user supplied input or pre-existing data. An optimization is performed for the set of dose objectives that results in an optimal dose distribution plan. Thereafter, a volumetric dose objective is generated based on the optimized dose distribution plan and displayed to the user (e.g., in a graphical user interface). The user is able to deform the volumetric dose objective via user input received over a period of time, during which the display of the volumetric dose objective is adjusted responsive to the user input in real-time while the input is received until the deformation operation ends.

In an embodiment, the user is able to effect a deformation using a "drag" operation executed by actuating a user input device at a first position, maintaining the actuation while moving the input device to a second position, and releasing the actuation at the second position. The deformation is performed, with the volumetric dose objective being continuously updated and the resulting optimized dose distributions are displayed to the user, while the device is moving as long as actuation (via a button or other control mechanism) is maintained.

In an embodiment, a method for updating an initial volumetric dose includes automatically generating, in a processor of a computing device, an initial volumetric dose objective in a target area based on input data. Note that the input data includes an initial dose distribution. In addition, the method includes causing the display of a graphical image including the target area and the initial volumetric dose objective. It is noted that the graphical image is being displayed in a display device communicatively coupled to the computing device. The method also includes receiving user input via a user input apparatus. Note that the user input includes a first user action at a first position in the graphical image and a second user action at a second position in the graphical image. Furthermore, the method includes calculating a deformation of the initial volumetric dose objective based on the user input. It is noted that the deformation is beginning at a position of the initial volumetric dose objective corresponding to the first position and ending at a position of the initial volumetric dose objective corresponding to the second position. Moreover, the method includes updating the initial volumetric dose objective based on the deformation and the display to include a visualization of the deformation.

In another embodiment, the method as described in the previous paragraph, wherein the calculating the deformation includes calculating a volume with a radius between the first and second positions; and applying the deformation based on the volume. Note that the radius is relative to the distance between the first and second positions.

In yet another embodiment, the method as described in the second paragraph above, wherein the initial dose distribution includes a plurality of initial dose values mapped to a plurality of positions in the initial volumetric objective. In addition, the calculating the deformation includes automatically re-calculating a subset of the plurality of initial dose values in real time responsive to the user input while the user input is being received. Furthermore, the calculating the deformation includes calculating a line between the first and second positions; and automatically re-calculating the subset of the plurality of initial dose values corresponding to positions in the target area within a threshold distance of the line. It is noted that dose values for the positions in the target area within the threshold distance are automatically adjusted based on the proximity of the position to the line.

Further embodiments provide systems that includes a processor, memory, display device and user input device that collectively perform the execution and implementation necessary to performing automatic volumetric dose objective deformation during optimization based on user supplied input through user interaction of a graphical user interface. By utilizing the systems and methods described above, dose distribution optimization can be further adjusted during optimization, with automatic recalculation based on visual displays of a volumetric dose that allows a user to more accurately shape a dose distribution of a radiation application as desired.

BRIEF DESCRIPTION OF DRAWINGS

The accompanying drawings, which are incorporated in and form a part of this specification, illustrate embodiments of the disclosure and, together with the description, serve to explain the principles of the presently claimed subject matter:

DETAILED DESCRIPTION

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known processes, procedures, components, and circuits have not been described in detail as not to unnecessarily obscure aspects and features of the subject matter.

Portions of the detailed description that follow are presented and discussed in terms of a process. Although operations and sequencing thereof are disclosed in one or more figures herein (e.g., FIG. 1, FIG. 2) describing the operations of this process, such operations and sequencing are exemplary. Embodiments are well suited to performing various other operations or variations of the operations recited in the flowchart of the figure herein, and in a sequence other than that depicted and described herein.

Some portions of the detailed description are presented in terms of procedures, operations, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed operation, logic block, process, etc., is here, and generally, conceived to be a self-consistent sequence of operations or instructions leading to a desired result. The operations are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "writing," "including," "storing," "transmitting," "traversing," "associating," "identifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

While the following example configurations are shown as incorporating specific, enumerated features and elements, it is understood that such depiction is exemplary. Accordingly, embodiments are well suited to applications involving different, additional, or fewer elements, features, or arrangements.

Volumetric Dose Objective Deformation

Figure 1:
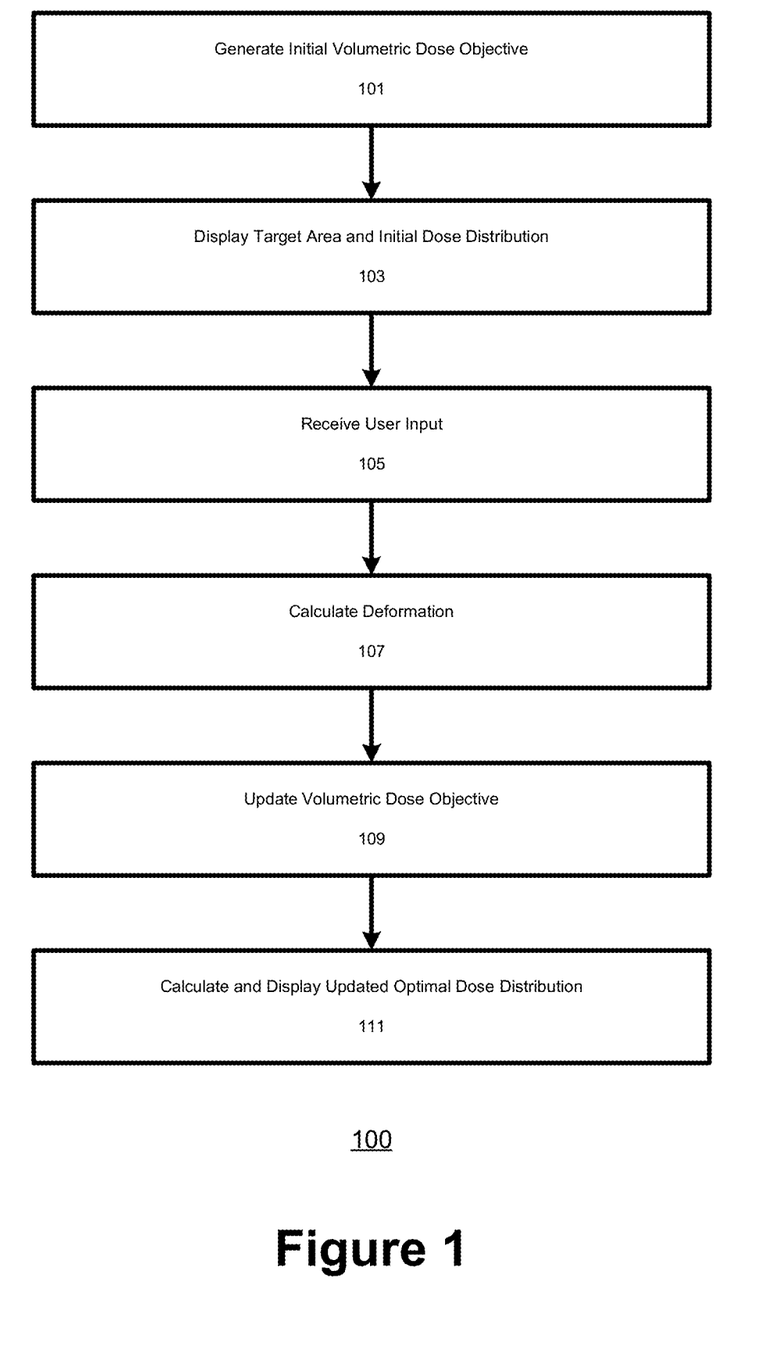
FIG. 1 depicts a flowchart for an exemplary process for calculating an updated volumetric dose objective during optimization, in accordance with embodiments of the present disclosure.

FIG. 1 depicts a flow chart illustrating an exemplary process performed by a computer system implementing automatic volumetric dose objective deformation, according to embodiments of the claimed subject matter. The process described with respect to FIG. 1 may be performed by any of the one or more computing systems described below with respect to FIG. 6. For example, in some embodiments, some or all of the steps of described process 100 are performed by any of a computing system operating as part of a treatment planning system or radiation application planning system. The process flow illustrated in FIG. 1 is provided for illustrative purposes only. Those skilled in the art will understand that one or more of the steps of the process illustrated in FIG. 1 may be removed or the order of the steps may be changed.

As depicted, the process 100 begins at step 101 through the generation of an initial volumetric dose objective. The initial volumetric dose objective may be generated based on an initial dose objective. The initial dose objective comprises one or more parameters and/or constraints that characterize or shape a dose distribution of a radiation application. These parameters may include, for example, a total dosage amount, position information in a target area, one or more identified structures or features in a target area, one or more coordinates in a target area, a maximum or minimum dosage limit for one or more structures, features, or coordinates, or any other characteristics of a distributed dose. In one or more embodiments, the parameters and/or constraints are expressed as values, which may be supplied by a user (via a user interface, for example), or referenced from pre-stored data. In one or more further embodiments, the values may be received as and/or extrapolated from a dose matrix, or dose-volume histogram, or the data used to generate a dose matrix and dose-volume histogram.

At step 103, a graphical visualization of the calculated dose distribution that results when the initial volumetric dose objective is used to optimize the treatment plan generated at step 101 is displayed in a display device. In one or more embodiments, the graphical visualization may be displayed proximate to an image of a target area in the radiation application subject. The image may be referenced from pre-existing computer-generated medical imaging data of the radiation application subject, during a pre-planning stage, for example. The graphical visualization may be projected, transposed, or overlaid over one or more portions of the image that correspond to positions in the target subject as specified by the initial dose objectives. According to further embodiments, the graphical visualization may be displayed as an outline of a two-dimensional area, for example.

The process continues at step 105 by receiving user input. User input may be received through, for example, at least a portion of a graphical user interface (e.g., user interface 300) using one or more user input devices. Alternately, where the display device comprises a touch-screen device, the user input may be received through contact with a suitable object at one or more positions of the touch-screen device. Additional embodiments may also include input received using virtual pointers in augmented reality or virtual reality devices. In one or more embodiments, the user input may consist of a user actuation at one or more positions in a display of a target area within the boundaries of the initial volumetric dose objective generated during step 101 and displayed at step 103. The user input received (e.g., registration of user actuation) at step 105 initiates a deformation operation at step 107.

The deformation operation is performed by calculating a deformation of the initial volumetric dose objective based on the user input received at step 105 (which may be a continuous user input over a period of time). Depending on the specific user input received, the dose objective values may be automatically adjusted to reflect an updated graphical representation of the volumetric dose objective at step 109, and the updated graphical representation is displayed in a display device for verification by the user. For example, a user input in the graphical user interface at some position outside of the initial volumetric dose objective may cause the deformation operation to warp a portion of the volumetric dose objective to fully encompass the position of the user input, and/or to extend in the direction of the position. Additional examples of user input and exemplary resultant deformations are described below with respect to FIG. 2.

Once the deformation operation is completed (e.g., via a subsequent actuation or a cessation of user input), the process continues at step 111 by calculating an optimal dose distribution for the updated volumetric dose objective. The optimal dose distribution is calculated by verifying the allocated dose values comply with dose parameters and constraints, and may also include readjusting the dose values to balance or redistribute dosage among targeted areas while still achieving dose objectives and remaining in compliance with dose constraints. In such a manner, a user is thus able to interactively shape (and view) the optimized calculated dose to ensure sufficient dose distribution coverage for all desired locations in a target.

Figure 2:
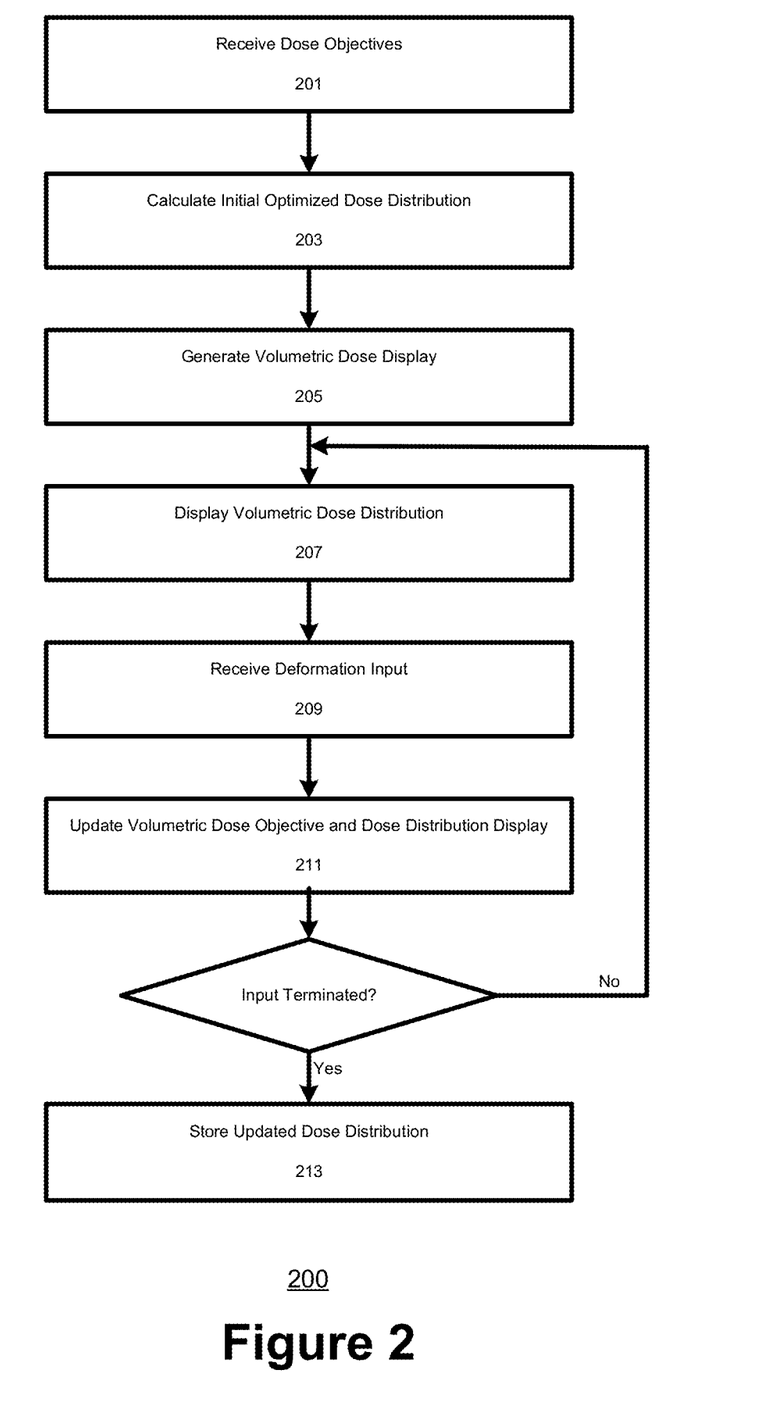
FIG. 2 depicts a flowchart for an exemplary process for calculating an updated dose distribution in real-time in response to user input, in accordance with embodiments of the present disclosure.

FIG. 2 depicts a flow chart illustrating an exemplary process 200 performed by a computer system implementing automatic volumetric dose objective deformation and visualization in real-time, according to embodiments of the claimed subject matter. The process described with respect to FIG. 2 may be performed by any of the one or more computing systems described below with respect to FIG. 6. For example, in some embodiments, some or all of the steps of described process 200 are performed by any of a computing system operating as part of a treatment planning system or radiation application planning system. The process flow illustrated in FIG. 2 is provided for illustrative purposes only. Those skilled in the art will understand that one or more of the steps of the process illustrated in FIG. 2 may be removed or the order of the steps may be changed.

As depicted, the process 200 begins at step 201 through the reception of one or more dose objectives. In one or more embodiments, the dose objectives may be entered by a user through a graphical user interface, or referenced from pre-stored data comprising, for example, a dose matrix, or dose-volume histogram, or other radiation planning data. At step 203, an initial dose distribution is automatically optimized and calculated by the computing system performing the process 200. Optimization may include, for example, calculating an optimal configuration for beam intensity and placement within a target subject to achieve the dose objectives received at step 201. Optimization may also include adjusting dose values to conform the spatial dose distribution to the target volume, and maximizing the gradient of the dose distribution outside the target.

A graphical visualization of a volumetric dose distribution is generated at step 205 based on the data values comprising the optimized dose distribution calculated at step 203, and displayed at step 207 to the user in a display device. In one or more embodiments, the graphical visualization may be displayed proximate to an image of a target area in the radiation application subject. The image may be referenced from pre-existing computer-generated medical imaging data of the radiation application subject, during a pre-planning stage, for example. The graphical visualization may be projected, transposed, or overlaid over one or more portions of the image that correspond to positions in the target subject as specified by the initial dose objectives. According to further embodiments, the graphical visualization may be displayed as an outline of a two-dimensional area, for example.

The process continues at step 209 by initiating a deformation operation based on received user input. User input may be received through, for example, at least a portion of a graphical user interface using one or more user input devices. Alternately, where the display device comprises a touch-screen device, the user input may be received through contact with a suitable object at one or more positions of the touch-screen device. In one or more embodiments, the user input may consist of a user actuation at one or more positions in a display of a target area within the boundaries of the initial volumetric dose distribution generated during step 203 and displayed at step 205. In one or more embodiments, any user input received (e.g., registration of user actuation) within the display of the target area and/or the volumetric dose objective automatically initiates a deformation operation.

In one or more embodiments, user actuation may be maintained over a distance in the display of the target area and over a period of time. For example, the user actuation may correspond to a "drag" operation in which a user actuates the user input device (e.g., via a user input device, a virtual/augmented user input interface, or registers a first contact point on a touch screen) at a first position, and moves the position of the user input device/contact point to an alternate position while maintaining actuation or without breaking contact with the touch screen. A subsequent release of the actuation/contact point terminates the deformation operation. In alternate embodiments, the deformation operation may be initiated and terminated by consecutive, separate actuations, without the need of maintaining an actuation.

According to one or more embodiments, the deformation is calculated as soon as the position of the actuation is modified or moved (dragged). Calculation of the deformation includes determining the positions in the target area corresponding to the user input, and calculating a modification of the volumetric dose objective based on the user input. The volumetric dose objective may be modified, for example, by warping or deforming a portion of the initial volumetric dose objective to encompass (via extension/protrusion) an additional, previously un-encompassed portion of the target area in the direction and/or area of the user input movement. In one or more embodiments, the degree of warping/extension is based on characteristics of the user input movement.

For example, where the user input corresponds to a direction away from the centroid of the initial volumetric dose objective, a portion of the initial volumetric dose objective in greatest proximity to the position of the user input is deformed in the same direction. Dose objective data values are automatically adjusted to accommodate the updated volumetric dose objective by re-distributing dose target values to account for the additional area. User input may continue to be received while the deformation operation is performed (e.g., via a subsequent actuation or a continuation of user input), the process continues at step 211 by calculating an updated volumetric dose objective using the updated dose objective values determined by calculating the deformation, and displaying the updated graphical representation of the optimized dose distribution to the user. According to one or more embodiments, steps 207 through 211 are repeated continuously in real-time during the entire period that user input corresponding to the deformation is received. By repeatedly calculating the updated dose values and updating the volumetric dose objective in real-time, the user is able to immediately visualize and intuitively recognize the effect on the volumetric dose objective (and by extension dose distribution) in response to the deformation effected based on the user input.

Once the deformation operation ends (e.g., based on a user actuation or a discontinuation of user input), the updated optimal dose distribution is stored at step 213 based on the final volumetric dose objective generated during the deformation operation. The updated optimal dose distribution may be calculated, for example, by verifying the allocated dose values comply with dose parameters and constraints, adjusting dose values to conform the spatial dose distribution to the target volume, and maximizing the gradient of the dose distribution outside the target. Other optimization techniques may also include readjusting the dose values to balance or redistribute dosage among targeted areas while still achieving dose objectives and remaining in compliance with dose constraints. In such a manner, a user is thus able to interactively shape (and view) the optimized calculated dose to ensure sufficient dose distribution coverage for all desired locations in a target.

Exemplary Graphical User Interface

Figure 3:
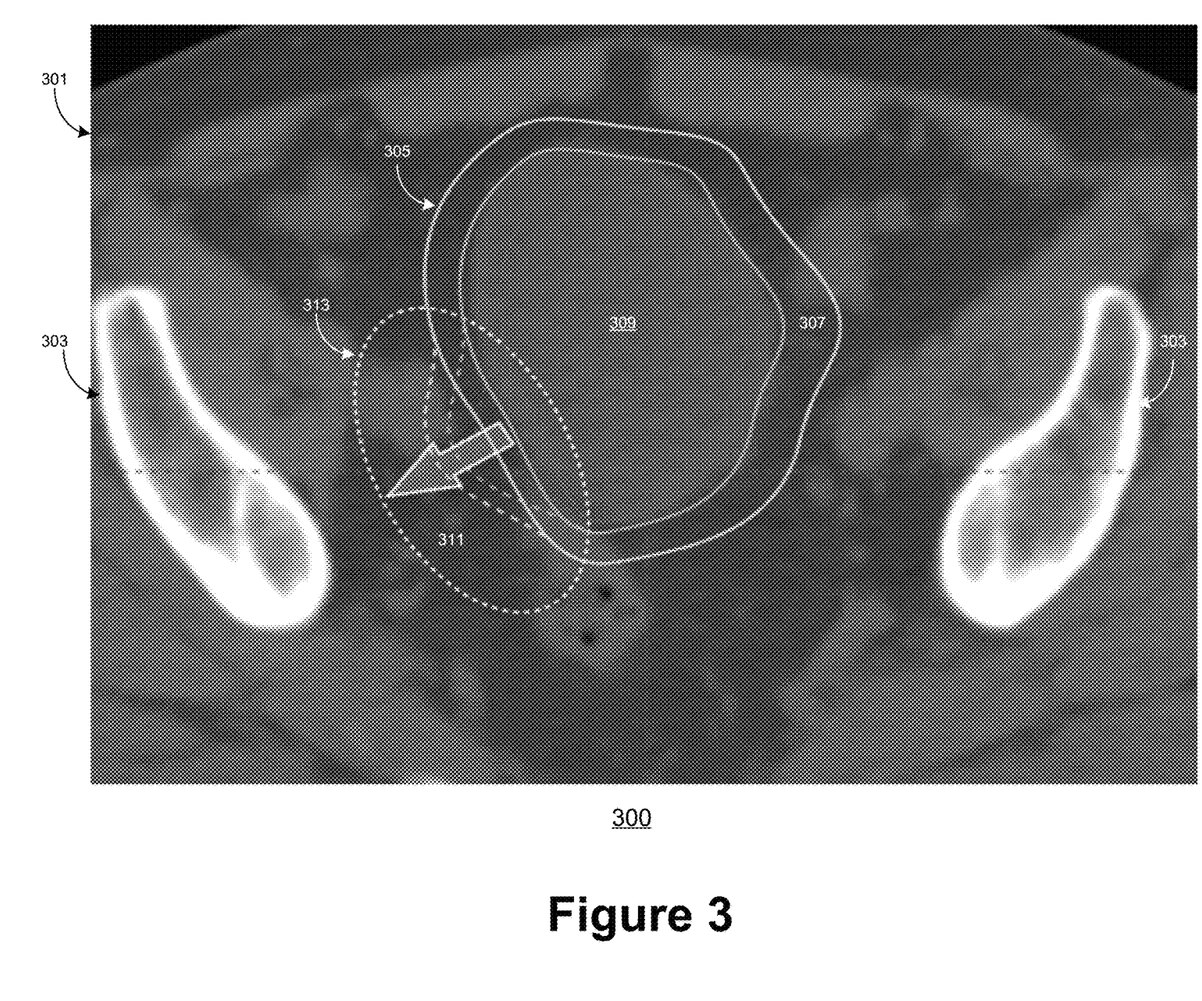
FIG. 3 depicts an exemplary graphical user interface that includes an optimized dose distribution, in accordance with embodiments of the present disclosure.

FIG. 3 depicts a portion of an exemplary graphical user interface, in accordance with one or more embodiments. As depicted, the graphical user interface may be implemented to include, for example, a display panel 300 configured to display a computer-generated image of a target area 301. In one or more embodiments, the image may be generated using image data acquired via one or more medical imaging techniques including, but not limited to, x-rays, magnetic resonance imaging (MRI), computer tomography (CT) scans, positron emission tomography (PET) scans, etc. The image data may be received as input from, for example, a memory or other storage device comprised in a computing device currently implementing an instantiation of the graphical user interface, or communicatively coupled to the computing device implementing the instantiation. According to other embodiments, the image data may also be received directly from one or more medical imaging devices. As depicted in FIG. 3, the panel 300 can also include a graphical overlay of a volumetric dose objective and optimized dose distribution calculated from an initial dose distribution, and based on (user-supplied) dose objectives.

As depicted in FIG. 3, the display panel 300 displays the image data of a target area. The display of the target area may include, according to various embodiments, one or more pre-identified structures 303, and one or more volumetric dose objectives (e.g., volumetric dose objectives 305, 307, and 309) generated based on calculated dose distributions. The dose distributions may be calculated based on a set of dose objectives. According to one or more embodiments, the dose distributions may be calculated from dose objectives submitted as user supplied input, or referenced from pre-existing configurations. The dose objectives themselves may consist partially or entirely of dose constraints (e.g., minimum/maximum dosage for specific targets) or other parameters that are used to calculate dose values for a dose application applied to the target area.

According to one or more embodiments, a user can effect a modification (deformation) of the volumetric dose objective directly through the graphical user interface. For example, if the user would like to extend the volumetric dose objective to encompass a structure or portion of a structure that is not included in the current volumetric dose objective visualization, the user can actuate a location within the volumetric dose objective, actuate a second location external to the volumetric dose objective at or proximate to the position in the target of interest, and a deformation operation is performed between the two locations actuated by the user. In one or more embodiments, actuation may be performed via a user input device such as a mouse, or a registration of a contact point on a touch screen (e.g., via a finger, stylus, or other suitable object).

According to further embodiments, the actuations may include a "press" actuation and a "release" actuation, similar to a "drag" operation performed via the user input devices. In one or more embodiments, the deformation is effected in a straight line between the two locations. As depicted in FIG. 3 for example, an arrow 311 indicates an exemplary drag operation, wherein the arrow point indicates the direction the drag operation is performed (e.g., the arrow in which the user input is moved). The dotted lines emerging from the solid line regions 305, 307, and 309 of the volumetric dose objective indicate respective new regions formed after the deformation is calculated and applied. According to alternate embodiments, the deformation may be implemented as a geometric shape 313 (such as a circle, rectangle, box, ellipse, etc.) that has as its diameter the straight line between the two locations.

According to still further embodiments, rather than a single constant deformation, each of the regions 305, 307, and 309 may have specific dose parameters/constraints that affect the degree to which deformation can be effected. According to such embodiments, the deformation calculated may be specifically adapted for each region individually. For example, an outer region (305) may be deformed to a greater (relative) degree when compared to the deformation applied to an inner region (307), which in turn may be deformed to a greater (relative) degree when compared to the deformation applied to the innermost region (309).

Figure 4A:
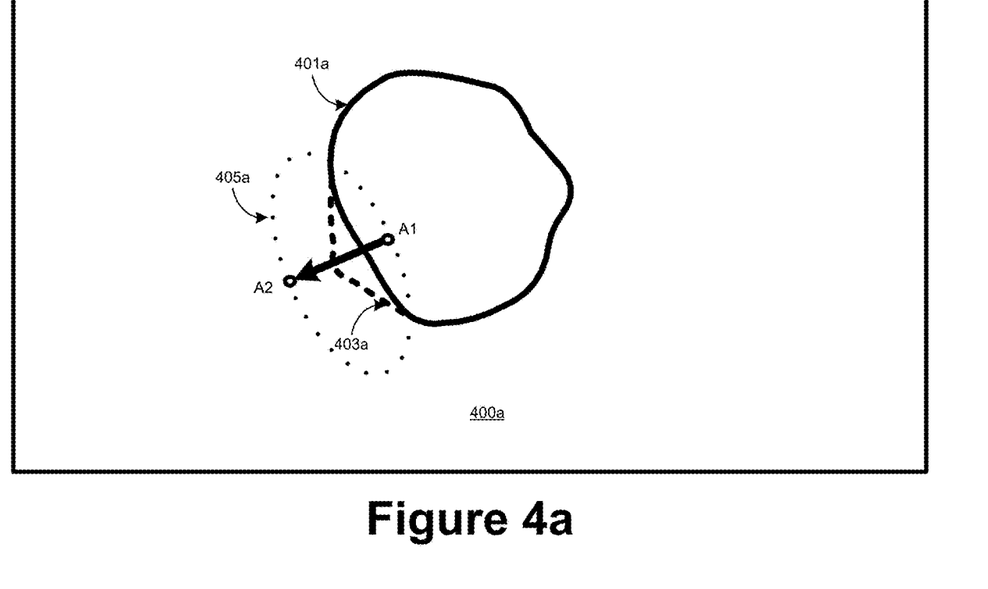
FIG. 4a depicts a diagram of an exemplary early deformation of a volumetric dose objective, in accordance with embodiments of the present disclosure.
Figure 4B:
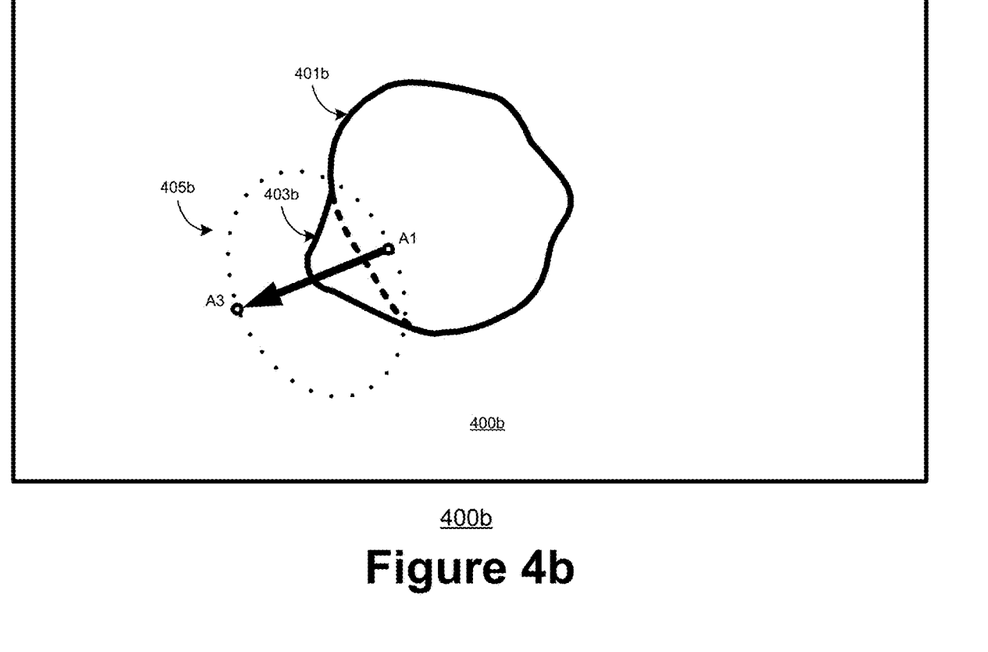
FIG. 4b depicts a diagram of an exemplary late deformation of a volumetric dose objective, in accordance with embodiments of the present disclosure.

FIGS. 4a and 4b depict diagrams 400a, 400b of an exemplary deformation of a volumetric dose objective at different stages of the deformation process, in accordance with embodiments of the present disclosure. FIG. 4a depicts an exemplary early-stage deformation of a single-level volumetric dose objective 401a within a target area, and can be displayed in a display panel such as the display panel 300 of a graphical user interface described above with respect to FIG. 3. As depicted in FIG. 4a, volumetric dose objective includes an initial volume (represented as the area contained in the solid line), an initial user input at time A1, and a current position of user input at time A2. As depicted, the volumetric dose objective 401a is deformed (according to the dotted line) based on the movement of the user input from time A1 to A2. The deformation includes an extension 403a of the area occupied by the volumetric dose objective 401a, applied (e.g., as an ellipsoid 405a) with a diameter that corresponds to the line (distance) between the two positions A1 and A2. In one or more embodiments, the deformation can be calculated and applied, and an updated volumetric dose objective can be displayed in real-time as the user input device is moved. Thus for example, A2 may correspond to a snapshot of a single movement away from A1 performed by the user input device.

FIG. 4b depicts the same volumetric dose objective 401b at a later stage, e.g., post deformation. As depicted, the volumetric dose objective 401b has been deformed based on the movement of the user input from time A1 to A3. A3 may correspond to the position at which a user actuation is received—or a user actuation is terminated—to complete the deformation operation (e.g., a release of a mouse button to terminate a drag operation). As depicted in FIG. 4b, the final volumetric dose objective 401b and the deformed area 403b extend further than the respective volumetric dose objective 401a and deformed area 403a at time A2 of FIG. 4a, which corresponds to an earlier point in time of the same deformation operation. As depicted, the deformation includes an extension 403b of the area occupied by the volumetric dose objective 401b, applied as an ellipse 405b with a diameter that corresponds to the line between the two positions A1 and A3.

Figure 5:
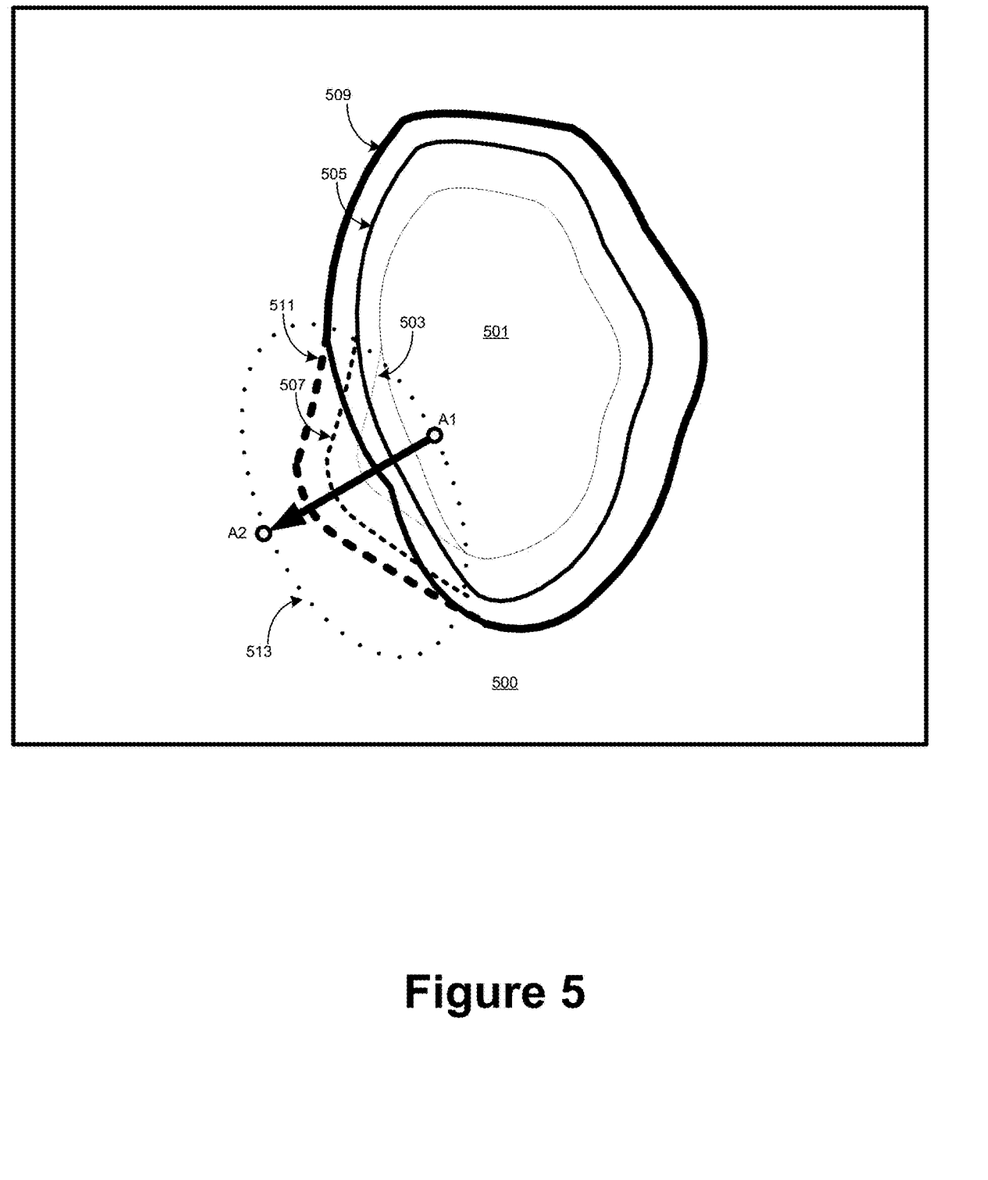
FIG. 5 depicts a diagram of an exemplary alternate volumetric dose objective after deformation during deformation, in accordance with embodiments of the present disclosure.

FIG. 5 depicts a diagram 500 of an alternate exemplary deformation of a volumetric dose objective at different stages of the deformation process, in accordance with embodiments of the present disclosure. FIG. 5 depicts an exemplary deformation of a single-level volumetric dose objective 501 within a target area, and can be displayed in a display panel such as the display panel 300 of a graphical user interface described above with respect to FIG. 3. As depicted in FIG. 5, volumetric dose objective includes an initial volume (represented as the area contained in the solid line), an initial user input at time A1, and a final position of user input at time A2. As depicted, the volumetric dose objective 501 is deformed (according to the dotted line) based on the movement of the user input from time A1 to A2. The deformation includes a penetration (via user input) and subsequent retraction 503 of the area occupied by the volumetric dose objective 501, applied as an ellipse 513 with a diameter that corresponds to the line between the two positions A1 and A2. In one or more embodiments, the deformation can be calculated and applied, and an updated volumetric dose objective can be displayed in real-time as the user input device is moved. Thus for example, A2 may correspond to a snapshot of a single movement away from A1 performed by the user input device. In one or more embodiments, the area removed during the deformation operation (503) may be graphically distinguished from the remaining portion of the volumetric dose distribution 501 after the operation is completed.

According to one or more embodiments, the rate and degree at which the volumetric dose objective is deformed is higher the longer the deformation operation is performed. That is, a weighted multiplier may be used to supplement the deformation values the greater the distance the deformation is extended. Such embodiments would result in a greater relative degree of deformation towards the terminal point in the deformation than deformation experienced at the position the deformation operation started (e.g., user actuation at A1). In alternate embodiments, the inverse is true. Thus, a weighted multiplier may be applied to dose values for positions having a greater proximity to the starting position, with the multiplier decreasing (e.g., linearly) the farther the deformation is extended from the beginning position. According to either embodiment, a user is able to specifically extend the volumetric dose objective to non-included targets and calculate dose values in response to the manual input automatically, for a more intuitive and more interactive experience.

Compared to conventional dose distribution optimization solutions, the claimed subject matter provides the ability to manually effect modifications to the volumetric dose objective through the graphical user interface using a user input device. All of the operations necessary for visually modifying a volumetric dose objective and re-calculating dose distributions in real-time and responsive to user input is combined in a single tool with an intuitive user interface design (exemplified by the graphical user interface depicted in FIG. 3). The graphical user interface is optimized for treatment planning optimization, and configured to perform the set of operations to process, generate, and create updated dose distributions from pre-existing and/or user supplied input, without the need to manually reinitiate dose distribution calculations.

The example features shown in FIGS. 3-5 are provided for illustrative purposes and is not to be construed as limiting. More or fewer elements (as well as different arrangements of those elements) than are shown in FIGS. 3-5 may be implemented in other embodiments. Further, the features described with respect to FIGS. 3-5 do not necessarily appear in all embodiments of the presently described innovations.

Exemplary Computer System

Figure 6:
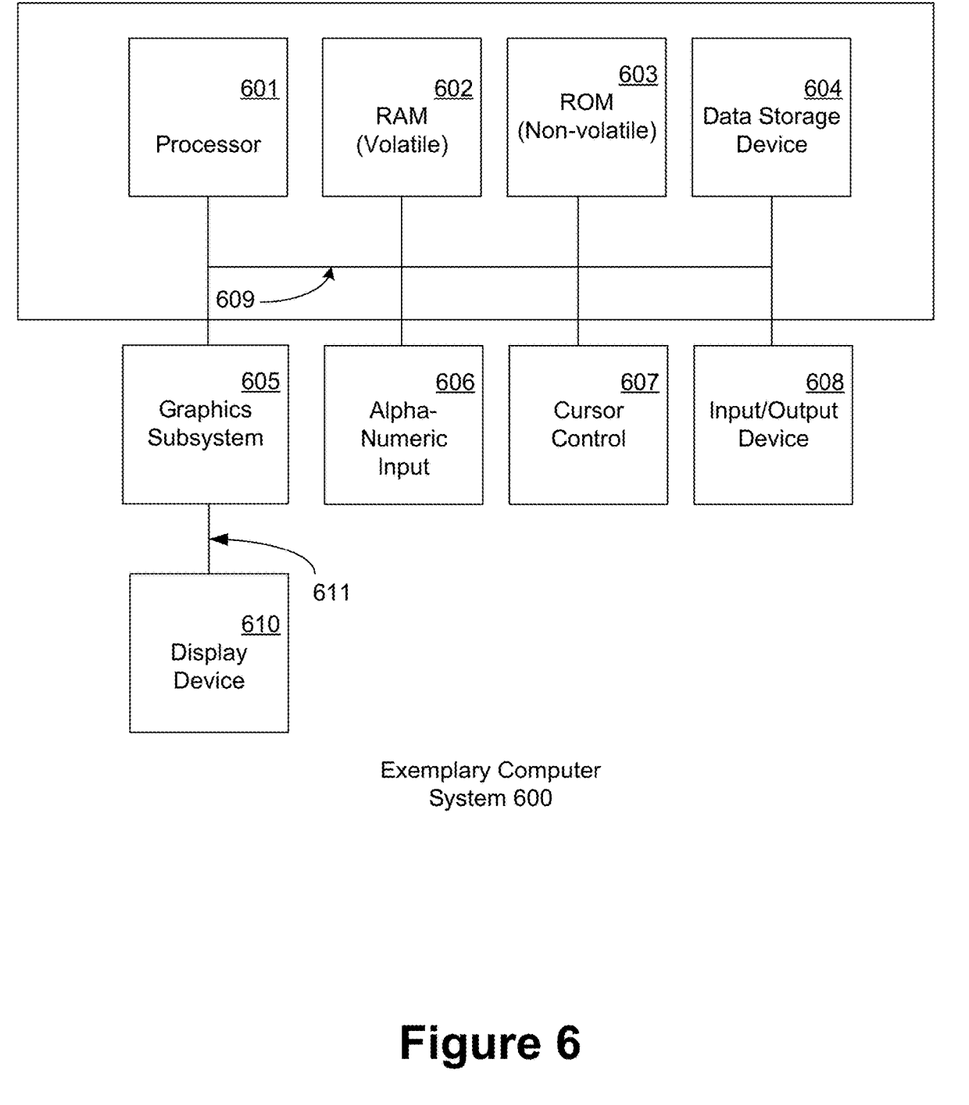
FIG. 6 depicts an exemplary computing environment, in accordance with embodiments of the present disclosure.

In one or more embodiments, the automated structure derivation described above with respect to FIGS. 1 and 2 may be executed as a series of programmed instructions and executed in a computing environment. FIG. 6 depicts such a computing environment, including computing system 600 upon which embodiments of the present invention may be implemented includes a general purpose computing system environment. In its most basic configuration, computing system 600 typically includes at least one processing unit 601 and memory, and an address/data bus 609 (or other interface) for communicating information. Depending on the exact configuration and type of computing system environment, memory may be volatile (such as RAM 602), non-volatile (such as ROM 603, flash memory, etc.) or some combination of the two.

The computer system 600 may also comprise an optional graphics subsystem 605 for presenting information to the radiologist or other user, e.g., by displaying information on an attached display device 610, connected by a video cable 611. In one or more embodiments, one or more of the graphical user interfaces described above with respect to FIGS. 3, 4*a*, 4*b*, and 5 may be rendered at least in part in optional graphics subsystem 605. Alternately, the graphical user interfaces may be rendered at least in part in processing unit 601. According to embodiments of the present claimed invention, the graphics subsystem 605 may be coupled directly to the display device 610 through the video cable 611. In alternate embodiments, display device 610 may be integrated into the computing system (e.g., a laptop or netbook display panel) and will not require a video cable 611. In one or more embodiments, one or more of the graphical user interfaces described above with respect to FIGS. 3, 4*a*, 4*b*, 5 may be displayed to a user in display device 610.

According to one or more embodiments, one or more of the storage of clinical data and the performance of the automatic structure derivation may be performed in one or more (distributed) computing systems remotely positioned relative to a display device upon which one or more instances of the graphical user interface described above is instantiated. For example, processing may be performed in one or more cloud computing centers using dynamically provisioned resources, with resulting displays presented in a local display and computing device of a user. Likewise, clinical data may be stored in one or more data stores which can be remotely positioned with respect to one or both of the local display and computing device of the user and the computing device performing the bulk of the processing for the automatic structure segmentation and the analysis of the clinical data.

Additionally, computing system 600 may also have additional features/functionality. For example, computing system 600 may also include additional storage (removable and/or non-removable) including, but not limited to, magnetic or optical disks or tape. Computer storage media includes volatile and nonvolatile, removable and non-removable media implemented in any method or technology for storage of information such as computer readable instructions, data structures, program modules or other data. RAM 602, ROM 603, and external data storage device (not shown) are all examples of computer storage media.

Computer system 600 also comprises an optional alphanumeric input device 606, an optional cursor control or directing device 607, and one or more signal communication interfaces (input/output devices, e.g., a network interface card) 608. Optional alphanumeric input device 606 can communicate information and command selections to central processor 601. Optional cursor control or directing device 607 is coupled to bus 609 for communicating user input information and command selections to central processor 601. Signal communication interface (input/output device) 608, also coupled to bus 609, can be a serial port. Communication interface 608 may also include wireless communication mechanisms. Using communication interface 608, computer system 600 can be communicatively coupled to other computer systems over a communication network such as the Internet or an intranet (e.g., a local area network).

Although the subject matter has been described in language specific to structural features and/or processological acts, it is to be understood that the subject matter defined in the appended claims is not necessarily limited to the specific features or acts described above. Rather, the specific features and acts described above are disclosed as example forms of implementing the claims.

What is claimed is:

1. A method for updating an initial volumetric dose, the method comprising:
   automatically generating, in a processor of a computing device, an initial volumetric dose objective including volumetric parameters, dose parameters and constraint parameters;
   causing the display of a graphical image including an image of an anatomic structure and a representation of a dose distribution based on the initial volumetric dose objective overlaid on a target area in the image of the anatomic structure in a display device communicatively coupled to the computing device, wherein the dose distribution includes a plurality of regions having different dose parameters or constraint parameters;
   receiving one or more user inputs associated with the representation of the dose distribution in the graphical image via a user input apparatus, the user input comprising a first user action at a first position in the dose distribution in the graphical image and a second user action at a second position in the dose distribution in the graphical image;
   calculating a deformation of the volumetric parameters and dose parameters of the initial volumetric dose objective based on the received one or more user inputs, the deformation beginning at a position of the initial volumetric dose objective corresponding to the first position and ending at a position of the initial volumetric dose objective corresponding to the second position, wherein the deformation is selected from the group consisting of:
      deforming an outer region of the dose distribution to a greater degree when compared to the deformation applied to an inner region of the dose distribution; and
      applying a weighted multiplier to dose values for positions having greater proximity to the first position, with the multiplier increasing or decreasing the further the deformation is extended from the first position to the second position; and
   updating the display of the graphical image including the image of the anatomic structure and the representation of the dose distribution based on the deformation of the volumetric dose objective overlaid on the target area in the image of the anatomic structure.

2. The method of claim 1, wherein the one or more user inputs comprise a drag operation, further wherein first and second user actions correspond to a beginning and end, respectively, of a single drag operation of the user input apparatus.

3. The method of claim 2, wherein the first user action comprises an actuation in a graphical user interface displaying the graphical image, wherein the actuation is performed via the user input apparatus, and the second user action comprises a release of the actuation in the graphical user interface performed via the user input apparatus, wherein the actuation of the user input apparatus is maintained between the first user action and the second user action.

4. The method of claim 1, wherein causing the display of a graphical image is performed on a computing device with a touch-sensitive screen, further wherein the one or more user inputs comprise one or more touch inputs on the touch-sensitive screen.

5. The method of claim 1, wherein the user input apparatus comprises at least one of:
   a mouse input device;
   a finger;
   a stylus;
   a virtual reality display device configured to generate a virtual user interface;
   an augmented reality display device configured to generate an augmented reality user interface; and
   a keyboard.

6. The method of claim 1, wherein updating the display of the graphical image is performed in real-time and is responsive to the one or more user inputs received between first and second user actions.

7. The method of claim 1, wherein calculating the deformation comprises:
   calculating a volume with a radius between first and second positions associated with the one or more user inputs; and
   applying the deformation based on the volume,
   wherein the radius is relative to the distance between the first and second positions.

8. The method of claim 1, wherein the volumetric dose objective comprises a plurality of regions, each of the plurality of regions corresponding to a dose level, further wherein calculating the deformation of the volumetric parameters and dose parameters comprises calculating a separate deformation for each of the plurality of regions.

9. The method of claim 1, wherein the one or more user inputs correspond to a single dose shaping operation, further wherein calculating the deformation, and updating the display of the graphical image is repeatedly performed over a course of the dose shaping operation.

10. The method of claim 1, wherein causing the display of a graphical image is performed on a computing device with a touch-sensitive screen.

11. The method of claim 1, wherein updating the display of the graphical image is performed in real-time.

12. The method of claim 1, wherein calculating the deformation comprises:
   calculating a volume with a radius between first and second positions associated with the one or more user inputs.

13. The method of claim 1, wherein the volumetric dose objective comprises a plurality of regions.

14. The method of claim 1, wherein the one or more user inputs correspond to a single dose shaping operation.

15. A system for creating a dose objective from a dose distribution, the system comprising:
   a memory device configured to store a set of programmed instructions and an image data;
   a user input device configured to receive a user supplied input, wherein the user input comprises a registration of an actuation by the user and, optionally, comprises a continuous input over time;
   a display device; and
   a processor configured to execute the programmed instructions to generate a display of the graphical user interface comprising a display of an image corresponding to the image data, wherein the processor is further configured:

to automatically generate an initial volumetric dose objective including volumetric parameters, dose parameters and constraint parameters, to cause the display of a graphical image including an image of an anatomic structure and a representation of a dose distribution based on the initial volumetric dose objective overlaid on a target area in the image of the anatomic structure in the display device, to receive one or more user inputs associated with the graphical image via the user input device including a first user action at a first position in the graphical image and a second user action at a second position in the graphical image, to calculate a deformation of the volumetric parameters and dose parameters of the initial volumetric dose objective beginning at a position of the initial volumetric dose object corresponding to the first position and ending at a second position based on the received on or more user inputs, wherein the deformation includes deforming an outer region of the dose distribution to a greater degree when compared to the deformation applied to an inner region of the dose distribution or applying a weighted multiplier to dose values for positions having greater proximity to the first position, with the multiplier increasing or decreasing the further the deformation is extended from the first position to the second position; and to update the display of the graphical image including the image of the anatomic structure and the representation of the dose distribution based on the deformation of the volumetric dose objective overlaid on the target area in the image of the anatomic structure.

16. The system of claim 15, wherein the user input device comprises at least one of:
   a stylus; and
   a keyboard.

17. The system of claim 15, wherein the one or more user inputs comprise a drag operation, further wherein a first and second actions correspond to a beginning and end, respectively, of a single drag operation of the user input device.

18. The system of claim 15, wherein the one or more user inputs comprise a drag operation.

19. The system of claim 15, wherein the user input device comprises a finger.

20. The system of claim 15, wherein the user input device comprises a mouse input device.

* * * * *